United States Patent
Gerusz et al.

(10) Patent No.: US 9,272,985 B2
(45) Date of Patent: Mar. 1, 2016

(54) ANTIBACTERIAL HYDROXYPHENYL COMPOUND

(75) Inventors: Vincent Gerusz, Paris (FR); Fabien Faivre, Paris (FR); Mayalen Oxoby, Paris (FR); Alexis Denis, Paris (FR); Yannick Bonvin, Paris (FR)

(73) Assignee: FAB PHARMA S.A.S., Paris (FR)

( * ) Notice: Subject to any disclaimer, the term of this patent is extended or adjusted under 35 U.S.C. 154(b) by 303 days.

(21) Appl. No.: 13/393,666

(22) PCT Filed: Nov. 11, 2009

(86) PCT No.: PCT/EP2009/064973
§ 371 (c)(1),
(2), (4) Date: Jun. 1, 2012

(87) PCT Pub. No.: WO2011/026529
PCT Pub. Date: Mar. 10, 2011

(65) Prior Publication Data
US 2012/0232155 A1    Sep. 13, 2012

Related U.S. Application Data

(60) Provisional application No. 61/238,995, filed on Sep. 1, 2009.

(51) Int. Cl.
*A61K 31/075* (2006.01)
*A61K 31/015* (2006.01)
*C07C 43/23* (2006.01)
*C07C 235/46* (2006.01)
*C07C 255/54* (2006.01)

(52) U.S. Cl.
CPC ............. *C07C 235/46* (2013.01); *C07C 255/54* (2013.01)

(58) Field of Classification Search
CPC ........................ C07C 235/46; C07C 255/54
See application file for complete search history.

(56) References Cited

U.S. PATENT DOCUMENTS

| | | | |
|---|---|---|---|
| 3,391,195 | A | 7/1968 | Blake et al. |
| 3,634,484 | A | 11/1972 | Traber et al. |
| 5,578,295 | A | 11/1996 | Francis et al. |
| 2006/0041025 | A1 | 2/2006 | Tonge et al. |
| 2010/0041658 | A1 | 2/2010 | Denis et al. |

FOREIGN PATENT DOCUMENTS

| | | |
|---|---|---|
| FR | 2 839 448 | 11/2003 |
| GB | 1 390 616 | 4/1975 |
| WO | WO 99/31036 | 6/1999 |
| WO | WO 00/35848 | 6/2000 |
| WO | WO 01/74753 A1 | 10/2001 |
| WO | WO 03/088913 A2 | 10/2003 |
| WO | WO 2004/043400 A2 | 5/2004 |
| WO | WO 2006/018723 A2 | 2/2006 |
| WO | WO 2006/071471 A2 | 7/2006 |
| WO | WO 2006/137840 A2 | 12/2006 |
| WO | WO 2007/027878 A2 | 3/2007 |
| WO | WO 2007/135562 | 11/2007 |
| WO | WO 2007/135562 A3 | 11/2007 |

OTHER PUBLICATIONS

International Search Report for PCT/EP2009/064973, mailed Mar. 17, 2010.
Written Opinion of the International Searching Authority for PCT/EP2009/064973, mailed Mar. 17, 2010.
Vel Leitner et al, "Kinetics and Mechanisms of the Photolytic and OH° Radical Induced Oxidation of Fluorinated Aromatic Compounds in Aqueous Solutions", Chemosphere, vol. 32, No. 5, pp. 893-906, 1996.
Form 1200 and claims filed Nov. 12, 2008 on entry of the European regional phase of PCT/IB2007/002127 (WO2007/135562), published as EP2010495 (15 pages).
Written Opinion of the International Searching Authority for PCT/IB2007/002127, mailed Nov. 2007.
International Search Report for PCT/IB2007/002127, mailed Nov. 12, 2007.

*Primary Examiner* — Zohreh Fay
(74) *Attorney, Agent, or Firm* — Nixon & Vanderhye P.C.

(57) ABSTRACT

The invention relates to a novel hydroxyphenyl compound, to the preparation of the compound and intermediates used therein, to the use of the compound as an antibacterial medicament and pharmaceutical compositions containing the compound.

20 Claims, No Drawings

ANTIBACTERIAL HYDROXYPHENYL COMPOUND

This application is the U.S. national phase of International Application No. PCT/EP2009/064973, filed 11 Nov. 2009, which designated the U.S. and claims the benefit to U.S. Provisional Application No. 61/238,995, filed 1 Sep. 2009, the entire contents of each of which are hereby incorporated by reference.

The invention relates to a novel hydroxyphenyl compound, to the preparation of the compound and intermediates used therein, to the use of the compound as an antibacterial medicament and pharmaceutical compositions containing the compound.

The invention particularly relates to a new compound capable of inhibiting bacterial and/or parasite fatty acid biosynthesis and the use of the compound as an antibacterial and/or antiparasitic agent.

The emergence of antibiotic-resistant pathogens has become a serious worldwide healthcare problem. Indeed, some infections are now caused by multi-drug resistant organisms that are no longer responsive to currently available treatments. There is therefore an immediate need for new antibacterial/antiparasitic agents with a novel mode of action.

The bacterial fatty acid biosynthesis (FASII system) has recently generated a lot of interest for the development of novel antibacterial/antiparasitic agents (Rock et al. *J. Biol. Chem.* 2006, 281, 17541; Wright and Reynolds *Curr. Opin. Microbiol.* 2007, 10, 447). The organization of components in the bacterial fatty acid biosynthesis pathway based on discrete enzymes is fundamentally different from the multifunctional FASI system found in mammals, therefore allowing good prospects of selective inhibition. The overall high degree of conservation in many enzymes of the bacterial FASII system should also allow the development of broader-spectrum antibacterial/antiparasitic agents.

Among all the monofunctional enzymes of the bacterial FASII system, FabI represents the enoyl-ACP reductase responsible of the last step of the fatty acid biosynthetic elongation cycle. Using the cofactor NAD(P)H as a hydride source, FabI reduces the double bond in the trans-2-enoyl-ACP intermediate to the corresponding acyl-ACP product. This enzyme has been shown to constitute an essential target in major pathogens such as *E. coli* (Heath et al. *J. Biol. Chem.* 1995, 270, 26538; Bergler et al. *Eur. J. Biochem.* 1996, 242, 689) and *S. aureus* (Heath et al. *J. Biol. Chem.* 2000, 275, 4654). However, other isoforms have been isolated such as FabK from *S. pneumoniae* (Heath et al. *Nature* 2000, 406, 145) and FabL from *B. subtilis* (Heath et al. *J. Biol. Chem.* 2000, 275, 40128). Although FabK is structurally and mechanistically unrelated to FabI (Marrakchi et al. *Biochem J.* 2003, 370, 1055), the similarity of FabI with FabL (*B. subtilis*), InhA (*M. tuberculosis*) and PfENR (*P. falciparum*) still offers opportunities of interesting activity spectra (Heath et al. *Prog. Lipid Res.* 2001, 40, 467).

Several FabI inhibitors have already been reported in the literature (Tonge et al. *Acc. Chem. Res.* 2008, 41, 11). Some of them such as diazaborines (Baldock et al. *Science* 1996, 274, 2107) and isoniazid in its activated form (Tonge et al. *Proc. Natl. Acad. Sci. U.S.A.* 2003, 100, 13881) act by covalently modifying the cofactor NAD+. However some drawbacks are associated with these products. Diazaborines are only used experimentally because of their inherent toxicity (Baldock et al. *Biochem. Pharmacol.* 1998, 55, 1541) while isoniazid is a prodrug restricted to the treatment of susceptible tuberculosis. The fact that isoniazid requires activation by hydrogen-peroxyde inducible enzymes (Schultz et al. *J. Am. Chem. Soc.* 1995, 117, 5009) enhances the possibilities of resistance by lack of activation or increased detoxification (Rosner et al. *Antimicrob. Agents Chemother.* 1993, 37, 2251 and ibid 1994, 38, 1829).

Other inhibitors act by interacting noncovalently with the enzyme-cofactor complex. For instance Triclosan, a widely used consumer goods preservative with broad spectrum antimicrobial activity, has been found to be a reversible, tight-binding inhibitor of *E. coli* FabI (Ward et al. *Biochemistry* 1999, 38, 12514). Intravenous toxicology studies on this compound indicated a $LD_{50}$ on rats of 29 mg/kg clearly ruling out intravenous injection (Lyman et al. *Ind. Med. Surg.* 1969, 38, 42). Derivatives based on the 2-hydroxydiphenyl ether core of Triclosan have been reported (Tonge et al. *J. Med. Chem.* 2004, 47, 509, *ACS Chem Biol.* 2006, 1, 43 and *Bioorg. Med. Chem. Lett.* 2008, 18, 3029; Surolia et al. *Bioorg. Med. Chem.* 2006, 14, 8086 and ibid 2008, 16, 5536; Freundlich et al. *J. Biol. Chem.* 2007, 282, 25436) as well as other inhibitors based on various classes of high throughput screening derived templates (Seefeld et al. *Bioorg. Med. Chem. Lett.* 2001, 11, 2241 and *J. Med. Chem.* 2003, 46, 1627; Heerding et al. *Bioorg. Med. Chem. Lett.* 2001, 11, 2061; Miller et al. *J. Med. Chem.* 2002, 45, 3246; Payne et al. *Antimicrob. Agents Chemother.* 2002, 46, 3118; Sacchettini et al. *J. Biol. Chem.* 2003, 278, 20851; Moir et al. *Antimicrob. Agents Chemother.* 2004, 48, 1541; Montellano et al. *J. Med. Chem.* 2006, 49, 6308; Kwak et al. *Int. J. Antimicro. Ag.* 2007, 30, 446; Lee et al. *Antimicrob. Agents Chemother.* 2007, 51, 2591; Kitagawa et al. *J. Med. Chem.* 2007, 50, 4710, *Bioorg. Med. Chem.* 2007, 15, 1106 and *Bioorg. Med. Chem. Lett.* 2007, 17, 4982; Takahata et al. *J. Antibiot.* 2007, 60, 123; Kozikowski et al. *Bioorg. Med. Chem. Lett.* 2008, 18, 3565), nevertheless none of these inhibitors have succeeded yet as a drug. Interestingly, some classes of these inhibitors display activity on both FabI and FabK: predominantly FabK for the dual compounds based on phenylimidazole derivatives of 4-pyridones (Kitagawa et al. *J. Med. Chem.* 2007, 50, 4710), predominantly FabI for the indole derivatives (Payne et al. *Antimicrob. Agents Chemother.* 2002, 46, 3118; Seefeld et al. *J. Med. Chem.* 2003, 46, 1627). However, the moderate activity on the second enzyme might prove to be a drawback for such compounds as it may lead to an increase of resistance mechanisms due to the added selection pressure (Tonge et al. *Acc. Chem. Res.* 2008, 41, 11).

Despite the attractiveness of FabI as an antibacterial/antiparasitic target, it is still largely unexploited at this time since there are no drugs on market or on advanced clinical phases.

WO 2007/135562 (Mutabilis SA) describes a series of hydroxyphenyl derivatives that display a selective spectrum of activity on species containing FabI and related targets, in contrast to Triclosan.

One of the purposes of the invention is to provide a novel compound active on FabI and related targets with improved pharmacological properties over existing compounds.

According to a first aspect of the invention, there is provided a compound of formula (I):

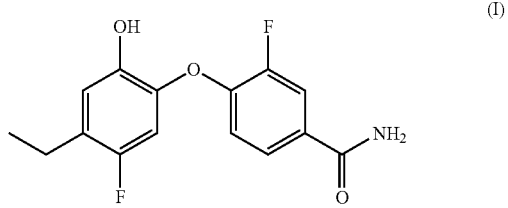 [SMILES: CCc1cc(O)c(Oc2ccc(C(N)=O)cc2F)cc1F]

or a pharmaceutically acceptable salt or solvate thereof.

The compound of formula (I) is known chemically as 4-(4-ethyl-5-fluoro-2-hydroxyphenoxy)-3-fluorobenzamide.

Thus, in one embodiment the compound of formula (I) is 4-(4-ethyl-5-fluoro-2-hydroxyphenoxy)-3-fluorobenzamide or a pharmaceutically acceptable salt or solvate thereof. In a further embodiment, the compound of formula (I) is 4-(4-ethyl-5-fluoro-2-hydroxyphenoxy)-3-fluorobenzamide.

The novel compound of the invention has good in vitro and in vivo activity and displays surprisingly greater solubility than previously described hydroxyphenyl derivatives as confirmed by data presented herein. Such increased solubility provides the significant advantage of allowing the compound of the invention to be administered intravenously. In particular, the compound of the invention is highly active in vitro against several pathogenic methicillin-susceptible *Staphylococcus aureus* (MSSA), methicillin-resistant *Staphylococcus aureus* (MRSA), vancomycin-intermediate *Staphylococcus aureus* (VISA) and vancomycin-resistant *Staphylococcus aureus* (VRSA) strains. Furthermore, the compound of the invention is also active in vivo in a murine model against MSSA, MRSA and VISA infections.

The compound of the invention exhibits high specificity and has no activity against other Gram-positive pathogens (*Streptococcus* and *Enterococcus*) which are not dependent upon FabI for fatty acid synthesis. In addition, the compound of the invention shows no cross resistance with glycopeptides (Vancomycin) and oxazolidinones (Linezolid) in target microbial populations. The target bacterial populations exposed to the compound of the invention exhibit only a low spontaneous mutation rate towards drug resistance (approximately $10^{-9}$) and, exhibit a bacteriostatic or slow bactericidal effect.

The compound of the invention also possesses an excellent safety profile. For example, during a detailed evaluation of the effects of the compound of the invention on the major physiological systems which included 112 in vitro binding assays and 42 in vitro enzyme assays, the compound of the invention was found to be devoid of any significant affinity or activity except in human norepinephrine transporter with 88% inhibition. In vitro, the compound of the invention produced a slight inhibition in hERG tail current amplitude up to 35.3% inhibition at 30 µM (after rundown subtraction), respectively. However, no QT interval prolongation was observed with the compound of the invention at any dose-levels in conscious dogs after a single intravenous infusion at 25, 50 and 100 mg/kg. Moreover, after the end of infusion with the compound of the invention, corrected QT was generally lower than in the control group. In a functional observation battery and in an evaluation of respiration function assays, the compound of the invention was well tolerated in rats with no relevant modifications compared to rats administered with vehicle only. Furthermore, during in vivo studies with the compound of the invention in rats and dogs, no major adverse effects were reported.

In the present context, the term "pharmaceutically acceptable salt" is intended to indicate salts which are not harmful to the patient. Such salts include pharmaceutically acceptable acid addition salts, pharmaceutically acceptable metal salts and pharmaceutically acceptable akaline addition salts. Acid addition salts include salts of inorganic acids as well as organic acids.

Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Representative examples of alkaline salts include, for example, sodium, potassium, lithium, calcium, magnesium or ammonium or organic bases such as, for example, methylamine, ethylamine, propylamine, trimethylamine, diethylamine, triethylamine, N,N-dimethylethanolamine, tris(hydroxymethyl)aminomethane, ethanolamine, pyridine, piperidine, piperazine, picoline, dicyclohexylamine, morpholine, benzylamine, procaine, lysine, arginine, histidine, N-methylglucamine.

The compound of formula (I) may be prepared by processes known to the skilled chemist to be applicable for preparing chemically related compounds. Such processes use known starting materials or intermediates which may be obtained by standard procedures of organic chemistry. The following process provides a non-limiting route for the production of the compound of formula (I) and intermediates used therein. This process constitutes a further feature of the invention.

According to a further aspect of the invention, there is provided a process (a) for preparing the compound of formula (I) as defined above, which comprises dealkylation of a compound of formula (II):

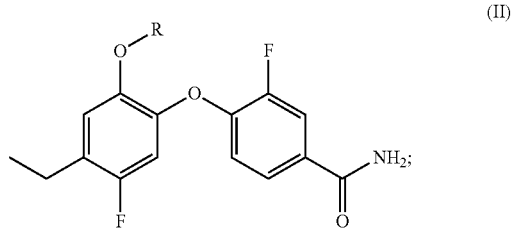

wherein R represents a $C_{1-6}$ alkyl group, such as methyl.

References herein to $C_{1-6}$ alkyl include any linear, branched or hydrocarbon groups having 1 to 6 carbon atoms, preferably methyl, ethyl, n-propyl, isopropyl, n-butyl, isobutyl and t-butyl, n-pentyl, isopentyl, neopentyl. In one particular embodiment, R represents methyl.

Process (a) typically comprises the use of a suitable dealkylating reagent, such as boron tribromide. Typically the process (a) is also conducted in the presence of a suitable solvent, such as dichloromethane.

The compound of formula (II) may be prepared in accordance with procedures described herein and is known herein as Intermediate 4 (D4).

According to a further aspect of the invention, there is provided a process (b) for preparing the compound of formula (I) as defined above which comprises acidic treatment of a compound of formula (III):

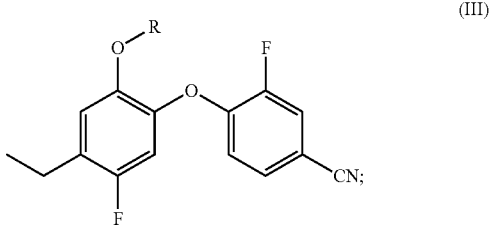

wherein R represents a $C_{1-6}$ alkyl group, such as methyl.

Process (b) typically comprises acidic treatment using suitable acids, such as acetic acid and sulphuric acid followed by purification with suitable agents, such as clarcel and charcoal in a suitable solvent, such as dichloromethane.

The compound of formula (III) may be prepared in accordance with procedures described herein and is known herein as Intermediate 3 (D3).

It will be appreciated that certain intermediates used in the synthesis of the compound of formula (I) may constitute additional aspects of the invention. For example, according to a further aspect of the invention there is provided an intermediate of compound (II)$^a$:

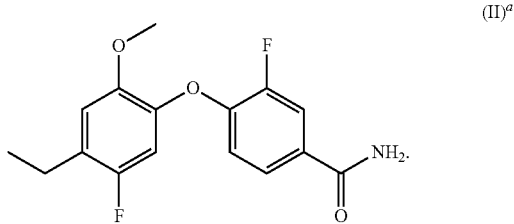 [SMILES: CCc1cc(OC)c(Oc2ccc(C(N)=O)cc2F)cc1F]

Furthermore, according to a further aspect of the invention there is provided an intermediate of compound (III)$^a$:

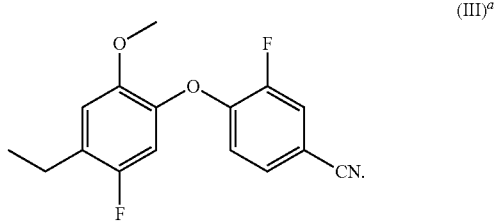 [SMILES: CCc1cc(OC)c(Oc2ccc(C#N)cc2F)cc1F]

As illustrated by the example given below, the hereinbefore disclosed compound of formula (I) has valuable biological properties. The compound is particularly useful as an antibacterial agent having a selective spectrum of activity in vitro and in vivo against bacterial strains relying on FabI and related targets. Such strains encompass *Staphylococcus aureus* including multiresistant strains (such as methicillin-susceptible *Staphylococcus aureus* (MSSA), methicillin-resistant *Staphylococcus aureus* (MRSA), vancomycin-intermediate *Staphylococcus aureus* (VISA) and vancomycin-resistant *Staphylococcus aureus* (VRSA) strains), *Acinetobacter baumannii, Bacillus anthracis, Chlamydophila pneumoniae, Escherichia coli, Haemophilus influenzae, Helicobacter pylori, Klebsiella pneumoniae, Neisseria meningitidis* and also bacteria such as *Mycobacterium tuberculosis* carrying homologous FabI enzymes such as InhA or other organisms such as *Plasmodium falciparum*. In one embodiment, the compound of the invention is used in the treatment of *Staphylococcus aureus* microbial infections including multiresistant strains such as methicillin-susceptible *Staphylococcus aureus* (MSSA), methicillin-resistant *Staphylococcus aureus* (MRSA), vancomycin-intermediate *Staphylococcus aureus* (VISA) and vancomycin-resistant *Staphylococcus aureus* (VRSA) strains.

The compound of formula (I) is therefore particularly suitable as an active principle of a medicament.

According to a further aspect of the invention, there is provided a compound of formula (I) as hereinbefore defined for use in therapy.

According to a further aspect of the invention, there is provided a pharmaceutical composition comprising a compound of formula (I) as hereinbefore defined, in association with a pharmaceutically acceptable excipient or carrier.

Said pharmaceutical compositions are advantageously formulated to be administered under oral, topical, parental including injectable routes, such as intravenous administration, with individual doses appropriate for the patient to be treated.

The compositions according to the invention can be solid, liquid or in the form of a gel/cream and be present in the pharmaceutical forms commonly used in human medicine, such as for example, plain or sugar-coated tablets, gelatin capsules, granules, suppositories, injectable preparations, ointments, creams, gels; they are prepared according to the customary methods. The active ingredient/s can be incorporated using excipients which are customarily used in these pharmaceutical compositions, such as talc, gum arabic, lactose, starch, magnesium stearate, aqueous or non-aqueous vehicles, fatty substances of animal or vegetable origin, paraffin derivatives, glycols, various wetting agents, dispersants or emulsifiers, preservatives. These compositions can also be present in the form of a powder intended to be dissolved extemporaneously in an appropriate vehicle, for example, non-pyrogenic sterile water.

In one embodiment, the pharmaceutical composition additionally comprises a solubilisation agent. In a further embodiment, the solubilisation agent is hydroxypropyl-beta-cyclodextrin (HPBCD), such as 20% HPBCD. HPBCD is a well known parenteral drug excipient and provides the advantage of being well tolerated in animals.

In one embodiment, the pharmaceutical composition additionally comprises an isotonic agent. In a further embodiment, the isotonic agent is glucose, such as 1% glucose monohydrate.

In one embodiment, the pharmaceutical composition additionally comprises a diluent. In a further embodiment, the diluents comprises water, such as QS water.

The dose administered varies according to the condition treated, the patient in question, the administration route and the product envisaged. It can, for example, be comprised between 0.01 g and 10 g per day, by oral route or by intramuscular or intravenous route in humans.

Said compositions are particularly useful to treat human or animal infections by microbial pathogens such as *Staphylococcus aureus* including multiresistant strains, *Acinetobacter baumannii, Bacillus anthracis, Chlamydophila pneumoniae, Escherichia coli, Haemophilus influenzae, Helicobacter pylori, Klebsiella pneumoniae, Neisseria meningitidis, S. intermedius, P. multocida, B. bronchiseptica, M. haemolytica* and *A. pleuropneumoniae.* and also bacteria such as *Mycobacterium tuberculosis* or other organisms such as *Plasmodium falciparum*.

Said compositions can also be useful in multitherapy, in combination with other medicaments, for example with antibiotics. It will be appreciated that such multitherapy may typically comprise either a composition comprising the compound of formula (I) additionally comprising one or more other medicaments, such as antibiotics or co-administration (i.e. sequential or simultaneous administration).

The invention therefore also relates to a method of treatment of microbial infections which comprises administering to a patient in need thereof an efficient amount of a compound of formula (I) as hereinbefore defined.

The invention also relates to a compound of formula (I) as hereinbefore defined for use in the treatment of microbial infections.

The invention also relates to the use of a compound of formula (I) as hereinbefore defined in the manufacture of a medicament for the treatment of microbial infections.

The invention also relates to a pharmaceutical composition comprising a compound of formula (I) as hereinbefore defined for use in the treatment of microbial infections.

EXAMPLES

Proton nuclear magnetic resonance ($^1$H NMR) spectra were recorded on a 400 MHz Brüker instrument, and chemical shifts are reported in parts per million downfield from the internal standard tetramethylsilane (TMS). Abbreviations for NMR data are as follows: s=singlet, d=doublet, t=triplet, q=quadruplet, m=multiplet, dd=doublet of doublets, dt=doublet of triplets, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray ionization (ESI) techniques on an Agilent 1100 Series LCMS. Analtech Silica Gel GF and E. Merck Silica Gel 60 F-254 thin layer plates were used for thin layer chromatography. Flash chromatography was carried out on Flashsmart Pack cartridge irregular silica 40-60 µm or spherical silica 20-40 µm. Preparative thin layer chromatography was carried out on Analtech Silica Gel GF 1000 µm 20×20 cm.

The meaning of certain abbreviations is given herein. ESI refers to electrospray ionization, M in the context of mass spectrometry refers to the molecular peak, MS refers to mass spectrometer, NMR refers to nuclear magnetic resonance and TLC refers to thin layer chromatography.

The starting materials are commercially available unless indicated otherwise.

Intermediate 1

1-(2-Fluoro-4-hydroxy-5-methoxyphenyl)ethanone (D1)

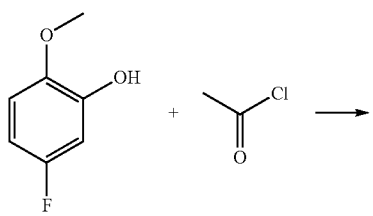

-continued

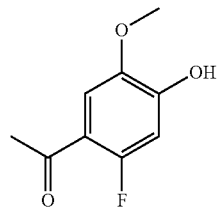

To a suspension of AlCl$_3$ (1.17 g; 8.79 mmol) in 1,2-dichloroethane (2 mL) was added acetyl chloride (0.55 g; 7.03 mmol). After 10 min stirring was added dropwise a solution of 5-fluoro-2-methoxyphenol (0.50 g; 3.52 mmol) in 1,2-dichloroethane (2 mL). The reaction mixture was stirred overnight at 40° C. The mixture was then poured on iced water and extracted with diethylether. The organic phases were combined, washed with brine, dried (Na$_2$SO$_4$) and concentrated to afford 582 mg (90%) of the title compound as an off-white solid.
MS (ES) m/e 185(M+H)$^+$
TLC: eluent cyclohexane/EtOAc 7/3 Rf=0.23
Intermediate 2 (via Clemensen Reduction)

4-Ethyl-5-fluoroguaiacol (D2)

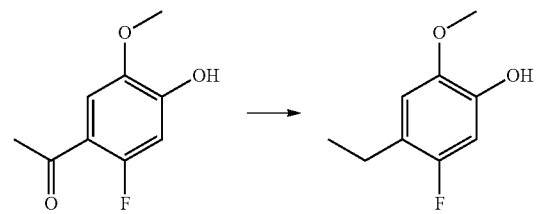

A solution of 1-(2-fluoro-4-hydroxy-5-methoxyphenyl)ethanone (18.0 g; 97.7 mmol; 1 eq; which may be prepared as hereinbefore described for D1) in glacial acetic acid (800 mL) is stirred at 70° C. before adding added zinc dust (63.9 g; 977 mmol; 10 eq). The resulting grey heterogeneous mixture is then heated at reflux and stirred overnight using a mechanical stirrer. After this period, zinc has aggregated and conversion rate reaches 90% according to the $^1$H NMR analysis of a crude aliquot. Therefore, the zinc metal is removed by filtration on a fritted glass and fresh zinc dust (6.4 g; 98 mmol) is added to the resulting limpid yellow filtrate. The solution is heated at reflux overnight until completion of the reaction. The solution is filtered on a fritted glass and basified until pH 11-12 is reached with a saturated aqueous solution of potassium carbonate (1.5 L) and with additional solid potassium carbonate if needed. The resulting aqueous layer is then extracted with ethyl acetate (1.0 L), dried over sodium sulphate or by azeotropic toluene distillation, filtered and concentrated under vacuum to afford the pure title compound (16.1 g; 94.7 mmol; 97%) as a pale yellow oil. It should be noted that the title compound is a volatile product and should be kept in the fridge under Argon away from light (darkens with oxygen and/or UV exposure).

Intermediate 2 (Via Catalytic Hydrogenation)

4-Ethyl-5-fluoroguaiacol (D2)

To a solution of 1-(2-fluoro-4-hydroxy-5-methoxyphenyl)ethanone (243 mg; 1.30 mmol; which may be prepared as hereinbefore described for D1) in absolute ethanol (3 mL) under argon is poured sulfuric acid 98% (10 μL; 0.13 mmol) and Pd/C 10% (137 mg; 0.06 mmol). The reaction mixture is flushed 3 times with hydrogen, and stirred 48 h under 5 bars of hydrogen.

Filtration over Celite, methanol wash and concentration of the filtrate affords the crude material which is further washed with saturated aqueous solution of NH$_4$Cl. Extraction of the aqueous phase with ethyl acetate, combination of the organic phases, drying (Na$_2$SO$_4$) and final concentration affords 186 mg (84%) of the title compound as a pale yellow oil. It should be noted that the title compound is a volatile product, should be kept in the fridge under Argon away from light (darkens with oxygen and/or UV exposure).

No or weak response in MS.

$^1$H NMR (DMSO), δ (ppm): 9.20 (bs, 1H), 6.78 (d, J=3.6 Hz, 1H), 6.54 (d, J=9 Hz, 1H), 3.73 (s, 3H), 2.50 (q, J=7.2 Hz, 2H), 1.12 (t, J=7.4 Hz, 3H)

Intermediate 3

4-(4-Ethyl-5-fluoro-2-methoxyphenoxy)-3-fluorobenzonitrile (D3)

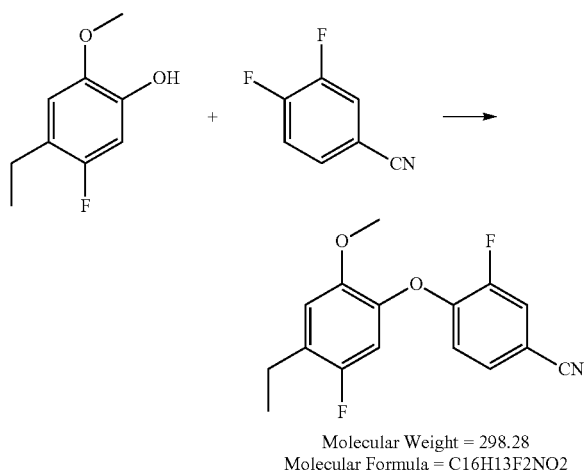

To a solution of 4-ethyl-5-fluoroguaiacol (8 g; 47 mmol) and 3,4-difluorobenzonitrile (6.53 g; 47 mmol; which may be prepared as hereinbefore described for D2) in 80 mL anhydrous acetonitrile is added potassium hydroxide (3.15 g; 56.4 mmol). The reaction mixture under argon atmosphere is stirred under reflux for 16 h. Concentration, addition of a saturated aqueous solution of ammonium chloride (100 mL), extraction with ethyl acetate (2*25 mL), reunification of the organic phases, brine wash (100 mL, drying (Na$_2$SO$_4$) and final concentration affords 12.95 g (95%) of the title compound as a brown solid.

MS (ES) m/e 290 (M+H)$^+$

TLC: eluent cyclohexane/EtOAc 7/3 Rf=0.74

Intermediate 3 (Alternative Procedure)

4-(4-Ethyl-5-fluoro-2-methoxyphenoxy)-3-fluorobenzonitrile (D3)

To 3,4-difluorobenzonitrile (12.26 g) dissolved in acetonitrile (10 volumes) was added 4-ethyl-5-fluoroguaiacol (15 g; which may be prepared as hereinbefore described for D2). Then, potassium hydroxide (0.33 parts) was added and the reaction mixture was refluxed for 7 hours. Once the reaction complete, the temperature was lowered to 20° C., water (2.5 volumes) was added and the phases separated. The organic phase was stored at RT until used in the next step.

Intermediate 4

4-(4-Ethyl-5-fluoro-2-methoxyphenoxy)-3-fluorobenzamide (D4)

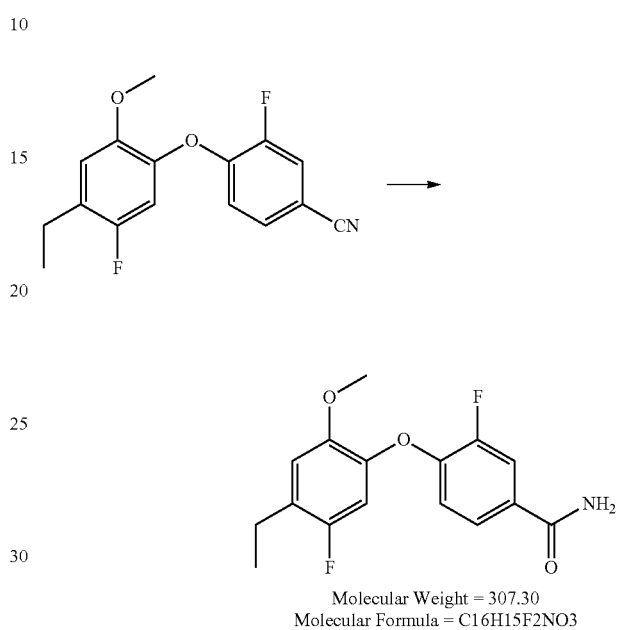

To 4-(4-ethyl-5-fluoro-2-methoxyphenoxy)-3-fluorobenzonitrile (12.95 g; 7.05 mmol; which may be prepared as hereinbefore described for D3) are added trifluoroacetic acid (52 mL) and concentrated sulfuric acid (13 mL). After 1 h 30 under reflux the reaction mixture is cooled down to room temperature and then poured down to iced water (400 mL).

Dichloromethane extraction (100 mL then 2*25 mL), reunification of the organic phases, saturated aqueous sodium hydrogenocarbonate wash (250 mL, pH=8-8.5), drying (Na$_2$SO$_4$) and final concentration affords 13.31 g (96%) of the title compound as an off-white solid.

MS (ES) m/e 294 (M+H)$^+$

TLC: eluent dichloromethane/methanol 9/1 Rf=0.3

Example 1

4-(4-Ethyl-5-fluoro-2-hydroxyphenoxy)-3-fluorobenzamide (E1)

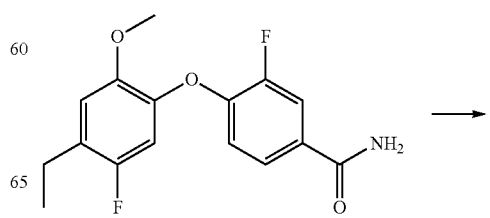

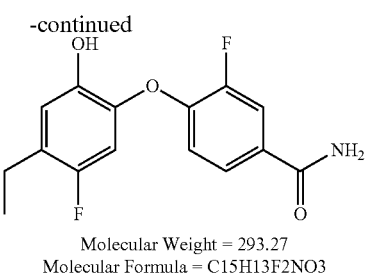

Molecular Weight = 293.27
Molecular Formula = C15H13F2NO3

To 4-(4-ethyl-5-fluoro-2-methoxyphenoxy)-3-fluorobenzamide (13.31 g, 4.59 mmol; which may be prepared as hereinbefore described for D4) in 130 mL of dichloromethane under argon at −78° C. under intense stirring is added over 15-20 min boron tribromide (130 mL at 1M in dichloromethane). The reaction mixture is warmed up at room temperature under stirring and after 3 h is cooled back to −20° C. for quenching with a saturated aqueous solution of ammonium chloride (100 mL). Partial concentration is performed to remove 170 mL of dichloromethane. 100 mL of ethyl acetate are added. Extraction of the aqueous phase (2*25 mL of ethyl acetate), reunification of the organic phases, aqueous sodium hydrogenocarbonate (200 mL at 1N) wash, drying (Na$_2$SO$_4$) and final concentration affords the crude material which is purified on silicagel (gradient dichloromethane/methanol:100/0→95/5) to afford the title compound 8.75 g (68%).

MS (ES) m/e 294 (M+H)$^+$

TLC: eluent dichloromethane/methanol 20/1 Rf=0.4

$^1$H NMR (DMSO), δ (ppm): 9.59 (s, 1H; OH); 7.95 (bs, 1H; NH); 7.80 (d, 1H, J=12.2 Hz); 7.63 (d, 1H, J=8.3 Hz); 7.40 (bs, 1H; NH); 6.96 (d, 1H, J=9.8 Hz); 6.87 (d, 1H, J=7.9 Hz); 6.78 (t, 1H, J=8.2 Hz); 2.56 (q, 2H, J=7.4 Hz); 1.17 (t, 3H, J=7.3 Hz).

Example 1

Alternative Procedure 4-(4-Ethyl-5-fluoro-2-hydroxyphenoxy)-3-fluorobenzamide (E1)

The solution of 4-(4-ethyl-5-fluoro-2-methoxyphenoxy)-3-fluorobenzonitrile (which may be prepared as hereinbefore described for D3) in acetonitrile was partially distilled under atmospheric pressure to 6.4 residual volumes. Then, 7 volumes of acetic acid were added and the solution was distilled under atmospheric pressure to 6.4 residual volumes. One additional volume of acetic acid was added and the solution was distilled again under atmospheric pressure to 6.4 residual volumes. Sulphuric acid (6 volumes total) was added and the reaction mixture was stirred at 120° C. for 5 hours. Once the reaction was complete, the temperature was lowered to 20° C., dichloromethane (10 volumes) and water (8 volumes) were added. At this temperature, clarcel (0.5 parts) and charcoal (0.5 parts) were also added and the resulting mixture was stirred for 30 min. The mixture was filtered and the intermediate cake washed three times with 2 volumes of dichloromethane each time. The resulting phases were separated and the aqueous phase was back extracted twice with 3 volumes of dichloromethane. The combined organic phases were partially distilled under atmospheric pressure to 14.5 residual volumes and methylcyclohexane (22 volumes) was added at 37° C.±2° C. To this solution was added sodium bicarbonate (10%) (1 volume). Instantaneous crystallization was observed. The slurry was cooled down to 0° C., filtered, washed twice with 2 volumes of methylcyclohexane at RT and dried at 40° C. under vacuum to afford the crude 4-(4-ethyl-5-fluoro-2-hydroxyphenoxy)-3-fluorobenzamide.

The crude 4-(4-ethyl-5-fluoro-2-hydroxyphenoxy)-3-fluorobenzamide was dissolved in 7 volumes of isopropanol and 1 volume of water at 60° C. to carry out a filtration on a zetacarbon cartridge. Then the cartridge was washed twice with 1 volume of isopropanol. Water (12.5 volumes) was added to this solution and the mixture was cooled down at 10° C./h to 5° C. The product was filtered, washed twice with water (2 volumes each time) at RT and dried under vacuum at 70° C. to afford the pure 4-(4-ethyl-5-fluoro-2-hydroxyphenoxy)-3-fluorobenzamide in 36.5% overall yield in 99.6% HPLC purity.

Comparative Example 2

5-Ethyl-4-fluoro-2-(2-fluoropyridin-3yloxy)phenol (E2)

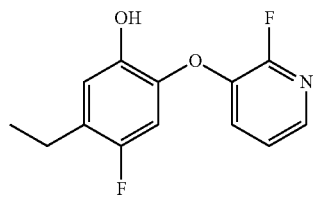 [SMILES: CCc1cc(O)c(Oc2cccnc2F)cc1F]

The title compound (E2) may be prepared as described in Example 87 of WO 2007/135562.

Example 3

Pharmaceutical Composition Comprising Example 1

Example 1 was dissolved in 20% HPBCD in 1% glucose solution at a concentration of 10 mg Example 1/ml and filled into 30 mL vials. The specific composition of Example 3 is as follows:

Example 1: 300 mg/vial
Glucose monohydrate: 330 mg/vial
HPBCD: 6000 mg/vial
Water for injection: QS 30.00 mL The following data was obtained for the compound of Example 1:

1. FabI Inhibition

The compound of the invention is a useful inhibitor of bacterial FabI enzyme.

Compound inhibitory activity of FabI enzyme is measured in vitro by the IC$_{50}$ determination using a fluorescence based assay.

The protein FabI from *S. aureus* is prepared and purified using standard methods for recombinant protein expression after cloning of the gene in a prokaryotic expression vector.

The biochemical activity of the FabI enzyme is assessed using the following method.

The assay buffer "AB" contained 50 mM ADA (N-(2-acetamido)iminodiacetic acid monosodium salt) pH 6.5, 1 mM dithiothreitol, 0.006% Triton-X100 and 50 mM NaCl. The following components are added in a white polystyrene Costar plate (Ref 3912) up to a final volume of 55.5 μL: 1.5 μL DMSO or inhibitor dissolved in DMSO and 54 μL of a FabI/NADPH/NADP+ mixture in AB. After 60 min of pre-incubation at room temperature, the reaction is started by addition of 5 μL of trans-2-octenoyl N-acetylcysteamine thioester (t-o-NAC) to a final volume of 60.5 μL. This reaction mixture is then composed of 2 nM FabI, 40 μM NADPH (Sigma, N7505), 10 μM NADP+ (Sigma, N5755), 100 μM t-O-NAC and compound at defined concentration. Fluorescence intensity of NADPH ($\lambda$ex=360 nm, $\lambda$em=520 nm) is measured immediately after t-O-NAC addition (T0), and approximately 50 min later (T50) by a Fluostar Optima (BMG) so as to achieve ±30% of NADPH conversion. Enzyme activity is calculated by first subtracting T0 signal to T50 and then subtracting background signal (FabI=0). Percentages of inhibition are calculated against untreated samples (Inhibitor=0) and $IC_{50}$ are fitted to a classical Langmuir equilibrium model using XLFIT (IDBS).

TABLE 1

In vitro inhibition of recombinant S. aureus and E. coli FabI enzyme by the compounds of Example 1 and Comparative Example 2

| FabI Inhibition $IC_{50}$ (μM) | S. aureus | E. coli |
|---|---|---|
| Example 1 | 0.012-0.014 | 0.058-0.068 |
| Comparative Example 2 | 0.008-0.017 | 0.019-0.065 |

The ranges shown in Table 1 indicate the results from a number of batches.

2. Antibacterial Activity

The compound of the invention is a useful antibacterial agent having a selective spectrum of activity in vitro against bacterial strains relying on FabI and related targets. Notably the compound of the invention shows activity against *Staphylococcus aureus* including multiresistant strains. The activity is presented as Minimum Inhibitory Concentration (MIC) expressed in μg/ml and was determined using broth microdilution or Agar dilution methods.

Strains

Antibacterial activity was determined on MSSA CIP 54.146 provided by the Centre de Ressources Biologiques de l'Institut Pasteur MIC Determination Using Broth Microdilution Method This protocol is compliant with Clinical Laboratory Standards Institute (CLSI) methodology as described in M7-A7 document of the CLSI. The compound to be tested is diluted according to a geometric series of reason 2 in pure DMSO. Dilutions are transferred in sterile polystyrene microplates, followed by mid-log phase bacteria in cation-adjusted Muller-Hinton broth (ca-MHB, Fluka, Reference 90922) with a final inoculum of $5\times10^5$ cfu/ml. Microplates are incubated overnight at 35° C. MIC is defined as the lowest concentration of antimicrobial agent that completely prevents visible bacterial growth. All manipulations, but compound handling (in pure DMSO), are performed under sterile conditions. The final concentration of DMSO in the plates is 2%.

TABLE 2

MIC (μg/ml) (Broth microdilution) of Example 1 and Comparative Example 2:

| Example | S. aureus CIP 54.146 |
|---|---|
| Example 1 | 0.063-0.125 |
| Comparative Example 2 | 0.063 |

The ranges shown in Table 2 indicate the results from a number of batches.

3. Solubility

One of the key advantages of the compound of the invention with respect to other FabI inhibitory compounds is to combine both excellent in vitro and in vivo activity with good solubility. Data has been generated which shows that Example 1 compares favourably in terms of pure aqueous solubility as well as formulated solubility to Comparative Example 2, a related compound displaying similar in vitro antibacterial activity.

For each medium, the saturation of the medium is obtained by adding an excess of investigated compound to a given volume of test medium. The suspension is stirred at 20° C. for 24 h, the supernatant is then isolated and diluted to allow its injection into a chromatographic system. The concentration of the compound in solution for each medium is determined by external standardization. The solubilisation results are shown in Tables 3 and 4.

TABLE 3

Aqueous solubility at pH 7.4 buffer:

| Compound | Solubility (μg/mL) |
|---|---|
| Example 1 | 16 |
| Comparative Example 2 | 8 |

The results in Table 3 show that the compound of the invention is two fold more soluble in pH 7.4 buffer than the comparative example 2.

Solubility was also investigated in a 20% hydroxypropyl beta cyclodextrin aqueous solution with 5% dextrose and the results are shown in Table 4.

TABLE 4

Formulated solubility in a 20% hydroxypropyl beta cyclodextrin aqueous solution with 5% dextrose:

| Compound | Solubility (mg/mL) |
|---|---|
| Example 1 | 11.3 |
| Comparative Example 2 | 2.4 |

The results in Table 4 show that the compound of the invention is almost 5 fold more soluble than the comparative example 2. Thus, the results shown herein demonstrate that Example 1 substantially retains the antibacterial potency shown by Comparative Example 2 but additionally has enhanced solubility.

4. Ascending Single Dose Study of the Safety, Tolerability, Pharmacokinetics and Pharmacodynamics of the Compound of Example 1

(a) Objectives

The primary objective of this study will be to assess the safety and tolerability of ascending single intravenous doses (SAD) in healthy adult subjects. The secondary objective of this study will be to determine the pharmacokinetic and pharmacodynamic (ex vivo serum antibiotic activity) preliminary profiles of the compound of Example 1.

(b) Study Design

This study will be a randomized, double-blind, placebo-controlled, inpatient/outpatient sequential ascending single doses in 7 cohorts of subjects (for the two first doses: 3 actives and 1 placebo, for other groups 6 actives and 2 placebos, following a randomization 3:1)

Safety schedule: Only 2 subjects could be dosed on the same day for the four first subjects. The 4 remaining subjects (for groups 3 to 7) could be dosed the same day. Nevertheless, the interval between each subject will be at least 10 minutes.

Depending on the safety results, additional cohorts may be explored, or progression of doses may be modified (intermediate dose level).

(c) Number of Subjects and Duration of Study

A sufficient number of subjects will be enrolled to allow 48 completed subjects in SAD. Each subject will participate in only 1 dose group. Subjects will be selected from healthy male volunteers 18 to 40 years of age, with a body weight=50 kg with a body mass index (BMI) calculated as weight in kg/(height in m$^2$) from 18 to 30 kg/m$^2$ at screening.

Each subject will participate in the study for maximum 3.5 weeks. Participation will include a screening evaluation within 3 weeks before administration of the formulation of Example 3, and a 3-day/2-night inpatient period (i.e. approximately 36 hours). The end-of-study evaluation will be conducted 72 hours after dosing.

It is estimated that each of the clinical parts (Part 1, Part 2) of the study will be completed in approximately 2 months.

(d) Study Drug, Dosages and Administration

The proposed study drug, dosages and administration are as shown in Table 5:

TABLE 5

Doses and Mode of Administration

| Name | Dose (mg) | Mode of Administration |
|---|---|---|
| Formulation of Example 3 | 10 mg od, 50 mg od, 100 mg od, 300 mg od, 600 mg od, 900 mg od, 1200 mg od | Once daily, intravenously using infusion pumps at a permanent flow rate of 1 ml/min |
| Placebo | n/a | Intravenously using infusion pumps at a permanent flow rate of 1 ml/min |

(e) Time Reference for Assessments

All time points are indicated with reference to the end of infusion Hend (i.e. Hend+0.5 is performed 30 minutes after the end of infusion).

Pre-dose refers to a time point immediately before the beginning of infusion, Intermediate refers to a time point half-way through the administration, both the start time and end time of infusion will be recorded.

(f) Safety Evaluation

Safety will be evaluated from reported signs and symptoms, scheduled physical examination findings, vital sign measurements, cardiac scope, digital 12-lead ECG readings, and clinical laboratory test results.

IV infusion local tolerability will be assessed using phlebitis scale, infiltration and Likert scales.

Subjects will come to the unit approximately 14 or 12 hours prior to administration of the drug. They will then remain in the clinical unit under permanent medical supervision and nursing for 24 hours after the end of infusion.

(g) Pharmacokinetics

Blood (15 ml) and urine (25 ml) samples will be obtained for the determination of the pharmacokinetic profile of the compound of Example 1 and its metabolites.

Groups 1 to 7: Blood samples for analytical determinations on Day 1: pre-dose, intermediate sampling (half-way through the infusion, except for Group 1 due to low duration of infusion), end of infusion Hend then Hend+0.5, +1, +2, +4, +6, +9, +12, +24, +48 and Hend+72 hours after the end of the infusion. Urine collection for analytical measurements pre-dose at H0 then H0 to Hend+24, Hend+24 to Hend+48.

All PK samples should be stored at −80° C. before analytical determinations.

(h) Pharmacogenetics

An additional blood sample (5 mL) will be collected for possible future pharmacogenetic studies related to absorption, distribution, metabolism, and/or excretion of the compound of Example 1. This sample is mandatory and will be collected prior to dosing (ie on Day 1 within 1 hour before dosing).

(i) Post Study Evaluation 72 hours after the (final) dosing, a clinical examination, vital signs, 12-lead digital ECG, routine laboratory tests will be evaluated. Following the completion of the study, a 3 months exclusion period will apply to the subject before he is allowed to take part in another clinical trial.

(j) Statistical Analysis

Single dose PK parameters will be derived from the plasma concentration time and urinary excretion data.

A compartmental or non-compartmental PK method, as appropriate, will be used to analyze the plasma and urine concentrations of the compound of Example 1 and its metabolites.

Pharmacodynamic parameters will be expressed in cfu/ml and calculation of area under the bacteriostatic titer curve and under the bactericidal titer curve (for 90, 99, and 99.9% killing rates).

For safety criteria, descriptive statistics will be provided by dose group. Description of potentially clinically significant values will be performed by dose group for vital signs, ECG parameters and blood chemistry and haematology parameters.

Description of adverse events and treatment emergent adverse events will be performed by dose group.

We claim:
1. A compound of formula (I):

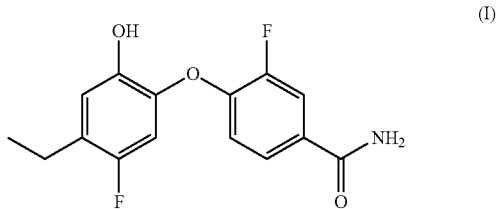 [SMILES: CCc1cc(O)c(Oc2ccc(C(N)=O)cc2F)cc1F]

or a pharmaceutically acceptable salt thereof.

2. A compound of formula (I) as defined in claim 1 which is 4-(4-ethyl-5-fluoro-2-hydroxyphenoxy)-3-fluorobenzamide.

3. A pharmaceutical composition comprising a compound of formula (I) as defined in claim 1, and a pharmaceutically acceptable excipient or carrier.

4. A pharmaceutical composition as defined in claim 3, which additionally comprises a solubilisation agent.

5. A pharmaceutical composition as defined in claim 3, which additionally comprises an isotonic agent.

6. A pharmaceutical composition as defined in claim 3, formulated to be administered under oral, topical, parental including injectable routes.

7. A pharmaceutical composition as defined in claim 3 comprising one or more other medicaments.

8. A method of treatment of microbial infections which comprises administering to a patient in need thereof an efficient amount of a compound of formula (I) as defined in claim 1.

9. A method as defined in claim 8 wherein said microbial infection is a human or animal infection by microbial pathogens selected from the group consisting of *Staphylococcus aureus* including multiresistant strains, *Acinetobacter baumannii*, *Bacillus anthracis*, *Chlamydophila pneumoniae*, *Escherichia coli*, *Haemophilus influenzae*, *Helicobacter pylori*, *Klebsiella pneumoniae*, *Neisseria meningitidis*, *S. intermedius*, *P. multocida*, *B. bronchiseptica*, *M. haemolytica* and *A. pleuropneumoniae*, *Mycobacterium tuberculosis* and *Plasmodium falciparum*.

10. A method as defined in claim 9 wherein said microbial infection is a human or animal infection by *Staphylococcus aureus* including multiresistant strains.

11. A process for preparing the compound of formula (I) as defined in claim 1, which comprises dealkylation of a compound of formula (II):

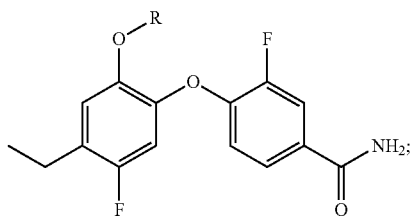

(II)

wherein R represents a $C_{1-6}$ alkyl group.

12. A compound of formula (II)$^a$:

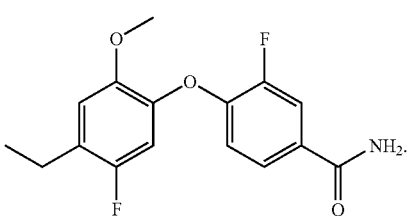

(II)$^a$

13. A process for preparing the compound of formula (I) as defined in claim 1, which comprises acidic treatment of a compound of formula (III):

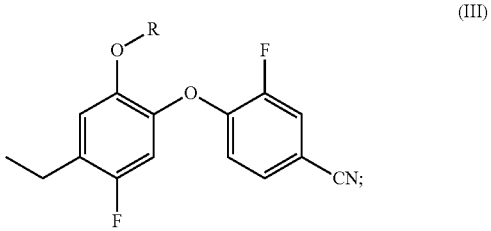

(III)

wherein R represents a $C_{1-6}$ alkyl group.

14. A compound of formula (III)$^a$:

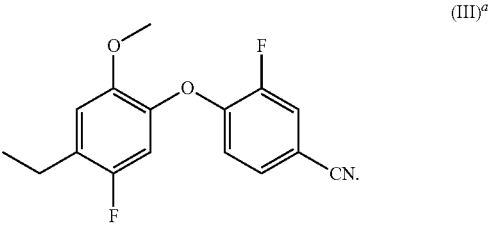 [SMILES: CCc1cc(OC)c(Oc2ccc(C#N)cc2F)cc1F]

(III)$^a$

15. A pharmaceutical composition as defined in claim 4, wherein the solubilisation agent is hydroxypropyl-beta-cyclodextrin (HPBCD).

16. A pharmaceutical composition as defined in claim 5, wherein the isotonic agent is glucose.

17. A pharmaceutical composition as defined in claim 7, wherein the one or more other medicament is an antibiotic.

18. A method as defined in claim 9, wherein the multiresistant *Staphylococcus aureus* strain is methicillin-susceptible *Staphylococcus aureus* (MSSA), methicillin-resistant *Staphylococcus aureus* (MRSA), vancomycin-intermediate *Staphylococcus aureus* (VISA) or vancomycin-resistant *Staphylococcus aureus* (VRSA) strains.

19. A process as defined in claim 11 wherein R represents methyl.

20. A process as defined in claim 13 wherein R represents methyl.

* * * * *